United States Patent [19]

Bózsing et al.

[11] Patent Number: 4,921,854
[45] Date of Patent: May 1, 1990

[54] CONDENSED THIAZOLOPYRIMIDINE, PYRIMIDO-THIAZINE OR THIAZEPINE PYRIMIDINE COMPOUNDS

[75] Inventors: Dániel Bózsing; Györgyi née Lax Kovànyi; Edit née Poldermann Berényi; Károly Magyar; Sándor Tuboly; Atti la Mándi, all of Budapest, Hungary

[73] Assignee: Egis Gyogyszergyar, Budapest, Hungary

[21] Appl. No.: 136,420

[22] Filed: Dec. 22, 1987

[30] Foreign Application Priority Data

Dec. 30, 1986 [HU] Hungary .............................. 5512/86
Dec. 30, 1986 [HU] Hungary .............................. 5514/86

[51] Int. Cl.$^5$ ..................... A61K 31/54; C07D 513/06
[52] U.S. Cl. .............................. 514/224.2; 514/258; 514/885; 514/48; 514/278
[58] Field of Search .................. 540/552; 544/48, 282, 544/278; 514/211, 222, 258, 224.2, 885

[56] References Cited

U.S. PATENT DOCUMENTS 4,485,107 11/1984 Kennis et al. ........................ 544/282
4,548,938 10/1985 Kennis et al. ......................... 544/48
4,609,660 9/1982 Doria et al. ......................... 544/278

FOREIGN PATENT DOCUMENTS 2032686 1/1972 Fed. Rep. of Germany ...... 544/278
2199581 7/1988 United Kingdom .................. 544/48

OTHER PUBLICATIONS

Sempuku, CA 94-30781 p (1981), "Thiazolo [3,2-a] Pyrimidine Derivatives".
Teijin Ltd. CA 94-30782 (1981), "Thiazolo [3,2-a] Pyrimidine Derivatives", Karl Thomae G.m.b.H., CA 64-8204.
"2-Aminodihydrothieno [3, 2-d]Pyrimidine" Mikhailov et al., CA 101-191835 n (1984), Reaction of 2-Mercaptopyrimidines with Some α, ω-dihaloalkanes.
Faskhutdinov et al., CA 109-162901 r (1989), "Analgesic and Antiinflammatory Efforts of Thiazolidinopyrimidinium and Pyrimidothiazinium Salts".
Dr. Karl Thomae, CA 64-8204 f (1966), "2-Aminodihydrothieno [3,2-d] Pyrimidine."
Teijin Ltd., Ca 94-30782 q, "Thiazolo [3,2-a] Pyrimidine Derivatives".
Teijin Ltd., Ca 94-30781 p eq. JP'591, "Thiazolo [3,2-a] Pyrimidine Derivatives".

Primary Examiner—Cecilia Shen
Attorney, Agent, or Firm—Keil & Weinkauf

[57] ABSTRACT

The compounds of the general formula I

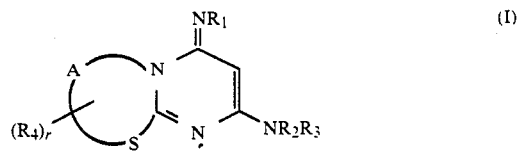

and pharmaceutically acceptable acid addition salts and hydrates thereof possess useful immunostimulant properties and can be used in therapy.

In the general Formula I
A stands for $-CH_2-CH_2-$, $-CH_2-CH_2-CH_2-$, $-CH_2-CH_2-CH_2CH_2-$ or $-CH=CH-$;
$R_4$ is hydrogen, $C_{1-4}$ alkyl or optionally substituted phenyl;
r is 0, 1, 2, 3 or 4;
$R_1$ stands for hydrogen of $C_{1-5}$ alkanoyl;
$R_2$ represents hydrogen, $C_{1-5}$ alkanoyl or a group of the general formula (a)

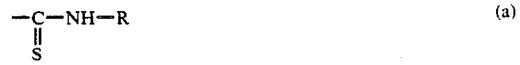

wherein
R stands for hydrogen, $C_{1-4}$ alkyl, $C_{2-4}$ alkenyl, phenyl or phenyl-$C_{1-3}$ alkyl and
$R_3$ stands for hydrogen.

The compounds of the general Formula I can be prepared by reacting a 2-mercapto-4,6-diamino-pyrimidine of the general Formula II

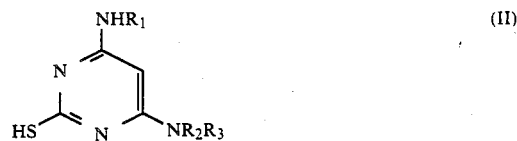

with a dihalo compound of the general Formula III

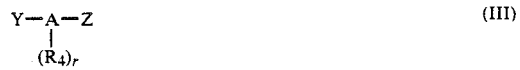

(wherein Y and Z are halogen).

13 Claims, No Drawings

CONDENSED THIAZOLOPYRIMIDINE, PYRIMIDO-THIAZINE OR THIAZEPINE PYRIMIDINE COMPOUNDS

This invention relates to new condensed pyrimidine derivatives, a process for the preparation thereof, pharmaceutical compositions comprising the same and new intermediates useful in the preparation of the said condensed pyrimidine derivatives and also a process for the preparation of the said intermediates.

In UK Pat. No. 1,072,414 thiazole[3,2-a]pyrimidine derivatives are disclosed. These compounds are reported to act on the circulation and to have sedative-tranquilizing, diuretic, cytostatic, bacteriostatic, antiinflammatory and antipyretic effect.

In Jpn.K. Tokyo 80,64,591 dioxo derivatives of thiazolo[3,2-a]pyrimidines having immunomodulating effect are described.

It is known that one of the fundamental objects of the prevention of infectious diseases resides in the increase of the efficiency of immunoprophylaxis and in the formation of homogenous immune condition in large populations. Compounds which are capable of stimulating the immune system provide useful assistance in the said efforts.

It is an object of the present invention to provide new condensed pyrimidine derivatives having improved immunostimulant activity.

According to an aspect of the present invention there are provided new condensed pyrimidine derivatives of the enral Formula I

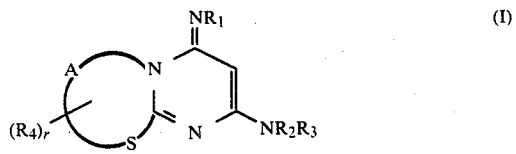

(wherein
A stands for $-CH_2-CH_2-$, $-CH_2-CH_2-CH_2-$, $-CH_2-CH_2-CH_2-CH_2-$ or $-CH=CH-$;
$R_4$ is hydrogen, $C_{1-4}$ alkyl or optionally substituted phenyl;
r is 0, 1, 2, 3 or 4;
$R_1$ stands for hydrogen or $C_{1-5}$ alkanoyl;
$R_2$ represents hydrogen, $C_{1-5}$ alkanoyl or a group of the general Formula (a)

wherein
R stands for hydrogen, $C_{1-4}$ alkyl, $C_{2-4}$ alkenyl, phenyl or phenyl-$C_{1-3}$ alkyl and
$R_3$ stands for hydrogen)
and pharmaceutically acceptable acid addition salts thereof and hydrates of the compounds of the general Formula I or pharmaceutically acceptable acid addition salts thereof.

Compounds of the general Formula I wherein $R_1$, $R_2$ and $R_3$ each stand for hydrogen can e present in two tautomeric forms as shown i Scheme A.

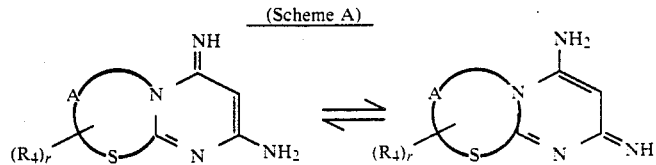

In the Formulae "A", $R_4$ and r are as stated above.

It has been found that the new compounds of the general Formula I increase cellular immune response to a significant extent, possess an immune stimulant effect and do not show any incompatibility with the vaccines used.

the term "$C_{1-4}$ alkyl" relates to straight or branched chain saturated aliphatic hydrocarbon groups (e.g. methyl, ethyl, n-propyl, isopropyl, n-butyl etc.). $R_4$ as phenyl may optionally bear one or more identical or different substituents (e.g. halogen, nitro, lower alkyl or lower alkoxy).

The term "$C_{1-5}$ alkanoyl" relates to acid radicals and the said groups are derived from aliphatic carboxylic acids having 1-5 carbon atoms (e.g. formyl, acetyl, propionyl, butyryl etc.). The term "$C_{2-4}$ alkenyl" relates to straight or branched chain aliphatic hydrocarbon groups comprising an olephinic double bond (e.g. vinyl, allyl, methallyl etc.). The "phenyl-$C_{1-3}$ alkyl group" may be e.g. benzyl or $\beta$-phenyl-ethyl. "A" stands for 1,2-ethylene, 1,3-propylene, 1,4-butylene or vinyl.

Compounds of the general Formula I, wherein A stands for $-CH_2-CH_2-$ or $-CH_2-CH_2-CH_2-$; $R_4$ stands for hydrogen or methyl; r is 1; $R_1$ and $R_3$ stand for hydrogen and $R_2$ is hydrogen or a group of the general Formula (a), in which R represents ethyl, and pharmaceutically acceptable acid addition salts thereof possess particularly valuable pharmaceutical properties.

Particularly preferred representatives of the compounds of the general Formula I are the following derivatives:

7-amino-5-imino-2,3-dihydro-5H-thiazolo[3,2-a]pyrimidine;

8-amino-6-imino-3,4-dihydro-2H,6H-pyrimido[2,1-b][1,3]thiazine;

8-amino-6-imino-3-methyl-2H,6H-pyrimido[2,1-b][1,3]-thiazine;

N-ethyl-N'-(5-imino-2,3-dihydro-5H-thiazolo[3,2-a]pyrimidine-7-yl)-thiourea and pharmaceutically acceptable acid addition salts thereof.

The pharmaceutically acceptable acid addition salts of the compounds of the general Formula I can be formed with inorganic or organic acids (e.g. hydrohalides such as hydrochlorides or hydrobormides; carbonates, hydrogen carbonates, sulfates, acetates, fumarates, maleates, citrates, ascorbinates etc.).

According to a further aspect of the present invention there is provided a process for the preparation of the compounds of the general Formula I and pharmaceutically acceptable acid additions salts and hydrates thereof, which comprises (a) reacting a 2-mercapto-4,6-diamino-pyrimidine derivative of the general Formula II

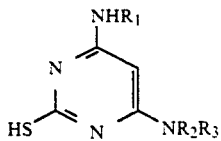 (II)

(wherein $R_1$, $R_2$ and $R_3$ are as stated above) with a dihalo compound of the general Formula III

 (III)

(wherein Y stands for halogen, preferably bromine; Z is halogen, preferably chlorine or bromine and A, $R_4$ and r are as stated above); or (b) reacting a 2-mercapto-4,6-diamino-pyrimidine derivative of the general Formula II with a diahlo compound of the general Formula III and subjecting the compound of the general Formula IV

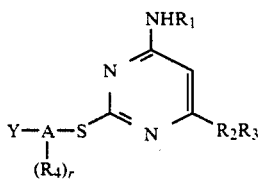 (IV)

thus formed (wherein A, $R_1$, $R_2$, $R_3$, $R_4$, Y and r are as stated above) to cyclisation after isolation; or (c) reacting a compound of the general Formula I, wherein $R_1$ and/or $R_2$ stand(s) for hydrogen, with a carboxylic acid of the general Formula V $$R_5-COOH \quad (V)$$

(wherein $R_5$ is hydrogen or $C_{1-4}$ alkyl) or a reactive derivative thereof; or (d) reacting a compound of the general Formula I, wherein $R_2$ stands for hydrogen, with an isothiocyanate of the general Formula VI $$R-N=C=S \quad (VI)$$

(wherein R is as stated above); or (e) reacting a compound of the general Formula VII

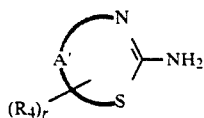 (VII)

(wherein A' stands for $-CH_2-CH_2-$ or $-CH=CH-$ and $R_4$ and r are as stated above) with malonic dinitrile of the Formula VIII;

$$NC-CH_2-CN \quad (VIII)$$

and, if desired, converting a compound of the general Formula I into a pharmaceutically acceptable acid addition salt thereof or setting free a base of the general Formula I from an acid addition salt thereof or transforming a compound of the general Formula I or a pharmaceutically acceptable acid addition salt thereof into a hydrate.

According to method (a) a 2-mercapto-4,6-diamino-pyrimidine of the general Formula II is reacted with a dihalo compound of the general Formula III. The reaction can be carried out in an inert organic solvent. As reaction medium e.g. a dialkyl amide (e.g. dimethyl formamide), dialkyl sulfoxide (preferably dimethyl sulfoxide), aliphatic alcohol (e.g. ethanol or isopropanol), chlorinated aliphatic hydrocarbon (e.g. chloroform, carbon tetrachloride, methylene dichloride), aromatic hydrocarbon (e.g. benzene, toluene, xylene), aliphatic ether (e.g. diethyl ether, tetrahydrofuran, dioxane), aliphatic hydrocarbon (e.g. hexane or petrol) or an aliphatic ketone (e.g. aceotne or methyl-ethyl-ketone) or a mixture of at least two of the above solvents can be used. It is particularly preferred to use dimethyl formamide as solvent. The reaction may be carried out in the presence of an acid binding agent. For this purpose e.g. an alkali carbonate (e.g. sodium or potassium carbonate), alkali hydrogen carbonate (e.g. sodium or potassium hydrogen carbonate), alkali hydroxide (e.g. sodium or potassium hydroxide), alkali earth metal hydroxide (e.g. calcium hydroxide) or a tertiary amine (e.g. pyridine, triethyl amine or an other trialkyl amine) can be used. Sodium carbonate and potassium carbonate are particularly useful as acid binding agent.

The starting materials of the general Formulae II and III can be used in equimolar amount or the dihalo compound of the general Formula III can be applied in a small excess of about 0.1-0.5 mole.

The reaction temperature depends on the reactivity of the starting materials. One may work generally at a temperature between room temperature and the boiling point of the reaction mixture, preferably at about 70° C.

The compounds of the general Formula I can be generally isolated in the form of an acid addition salt—preferably the hydrobromide—but other pharmaceutically acceptable acid addition salts can be formed as well.

According to method (b) of the process of the present invention a 2-mercapto-4,6-diamino-pyrimidine of the general Formula II is reacted with a dihalo compound of the general Formula III and the compound of the general Formula IV thus formed is subjected to cyclisation after isolation. The reaction can be carried out in a inert organic solvent and in the presence of an acid binding agent. The inert organic solvents and the acid binding agents, respectively, can be those enumerated in connection with method (a). The intermediates of the general Formula IV are formed at a lower temperature than that disclosed in method (a). One may work preferably at 30°-50° C., particularly at about 40° C. On the other hand, the reaction time of method (b) (formation of the compound of the general Formula IV and ring closure) is longer than that of method (a). The reaction time depends on the activity of the starting materials used and the temperature and is generally about 10-20 hours. Cyclisation of the compound of the general Formula IV can be accomplished at a higher temperature, preferably at a temperature between about 50° C. and the boiling point of the reaction mixture.

The reaction mixture can be worked up by methods known per se.

According to method (c) a compound of the general Formula I, wherein $R_1$ and/or $R_2$ stand(s) for hydrogen, is acylated with a carboxylic acid of the general Formula V or a reactive derivative thereof. As reactive acid derivative preferably the corresponding anhydrides, acid halides or esters can be used. Acylation is carried out by methods known per se. If acylation is accomplished with the aid of an acid chloride, one may preferably add an acid binding agent to the reaction mixture. For this purpose e.g. an alkali carbonate, alkali hydrogen carbonate, alkali hdyroxide or triethyl amine can be used. if an acid anhydride is used as acylating agent, the excess thereof can play the role of the reaction medium or one may work in the presence of an inert organic solvent. If free carboxylic acids of the general Formula V are used, acylation may preferably be carried out in the presence of a dehydrating agent (e.g. dicyclohexyl carbodiimide). Acylation may be carried out generally at a temperature between 10° C. and the boiling point of the reaction mixture, depending on the reactivity of the starting materials.

In the course of method (c) one or two acyl group(s) is (are) introduced into the molecule [i.e. the amino and/or imino group attached to the pyrimidine ring is (are) acylated] depending on the amount of the acylating agent used.

According to method (d) a compound of the general Formula I, wherein $R_2$ stands for hydrogen, is reacted with an isothiocyanate of the general Formula VI to yield a compound of the general Formula I, wherein $R_2$ represents a group of the general Formula (a). The reaction may be carried out in an inert organic solvent at a temperature between room temperature and the boiling point of the reaction mixture. As reaction medium preferably an alkanol (e.g. ethanol) can be used. The isothiocyanate of the general Formula VI can be used in a 1 -1.5 molar equivalent amount, related to the amino compound of the general Formula I.

According to method (e) of the process of the present invention compounds of the general Formula I, wherein $R_1$, $R_2$ and $R_3$ stand for hydrogen and A is $-CH_2-CH_2-$ or $-CH=CH-$, are prepared by reacting a compound of the general Formula VII with malonic dinitrile of the general Formula VIII. As reaction medium preferably the solvents enumerated in method (a) can be used with the exception of aliphatic ketones. It is particularly preferred to use an aliphatic alcohol as reaction medium. The reaction can be preferably carried out in the presence of a basic catalyst. For this purpose preferably alkali alcoholates (e.g. sodium methylate or sodium ethylate) can be used but the other bases enumerated in connection with process (a) can be applied as well.

The starting materials of the general Formulae VII and VIII can be used in equimolar amounts or the malonic dinitrile of the Formula VIII can be used in an excess of 0.1-0.5 moles.

The reaction can be accomplished at a temperature between room temperature and the boiling point of the reaction mixture, depending on the reactivity of the starting materials used.

The reaction mixture can be worked up by methods known per se.

The compounds of the general Formula I thus obtained can be converted into the acid addition salts thereof by methods known per se. Thus, the compound of the general Formula I can be reacted with the corresponding inorganic or organic acid in an inert organic solvent.

The compounds of the general Formula I can be set free from the said acid addition salts by treatment with a base in a manner known per se.

The compounds of the general Formula I and acid addition salts thereof can form hydrates. The said hydrates can either be obtained by adding water to a compound of the general Formula I or an acid addition salt thereof or can be spontaneously formed owing to the hygroscopic properties of the anhydrous compounds of the general Formula I.

According to a further aspect of the present invention there are provided new intermediates of the general Formula IV and acid addition salts thereof (wherein A stands for $-CH_2-CH_2-$, $-CH_2-CH_2-CH_2-$, $-CH_2-CH_2-CH_2CH_2-$ or $-CH=CH-$;

$R_4$ is hydrogen, $C_{1-4}$ alkyl or optionally substituted phenyl;

r is 0, 1, 2, 3 or 4;

$R_1$ stands for hydrogen or $C_{1-5}$ alkanoyl;

$R_2$ represents hydrogen, $C_{1-5}$ alkanoyl or a group of the general Formula (a), wherein R stands for hydrogen, $C_{1-4}$ alkyl, $C_{2-4}$ alkenyl, phenyl or phenyl-$C_{1-3}$ alkyl and $R_3$ stands for hydrogen;

Y stands of halogen).

According to a further aspect of the present invention there is provided a process for the preparation of compounds of the general Formula IV and salts thereof which comprises reacting a 2-mercapto-4,6-diamino-pyrimidine of the general Formula II (wherein $R_1$, $R_2$ and $R_3$ are as stated above) with a dihalo compound of the general Formula III (wherein Y stands for halogen, preferably bromine; Z is halogen, preferably chlorine or bromine and A, $R_4$ and r are as stated above) and, if desired, converting the compound of the general Formula IV thus obtained into an acid addition salt thereof.

The new intermediates of the general Formula IV can be prepared and converted after isolation into the compounds of the general Formula I as described in method (b).

The 2-mercapto-4,6-diamino-pyrimidines used as starting material are known compounds and can be prepared by a modified Traube-synthesis [W. Traube, Ann. 331, 64 (1904)].

The starting materials of the general Formula III, V, VI, VII and VIII are known compounds and readily available commercial products.

The compounds of the general Formula I possess valuable immunostimulant properties.

Exogenous regulation of the immunizing system, the correction of its hyperfunction or insufficiency, came into the foreground in the past decade, following the more detailed recognition of the immunological processes.

In a microbiological sense, immunity means the protection of the organism against pathogens (such as bacteria, viruses, fungi or parasites), or against their toxic materials. Any time the current state of immunity and formation thereof are influenced in addition to genetical properties also by biological effects of the environment. The cells of the immunity system work according to a strictly defined "division of labour", i.e., some have the faculty to recognize the foreign materials (antigens), others produce antibodies or become differentiated into reactive immunocites and some can also be found which coordinate and/or control the relationships between the defined groups of cells. On this basis immunity can also be characterized by the fact that the organism recognizes the materials foreign to it and is able to produce immunity responses towards them by a strictly determined cellular interaction.

From the viewpoint of prophylaxis against contagious diseases, the so-called "active immunity" created artificially by vaccination is extremely significant, when an "attenuated" variety of the pathogens, killed pathogens, or toxins thereof are ingested in the organism.

The immunogenic effects of the vaccines applied in immunoprophylaxis are rather varied. In the case of certain vaccines even life-long immunity can be achieved, some of them lend protection for 1–2 years and a very significant part of them results in an immunity lasting only for a few months.

In the past decade the recognition and practical application of materials modifying or stimulating immunity resulted in promising achievements and progress in respect of the correction of immunologic deficiency of the organism and in enhancing the efficiency of vaccines having only weak immunogenic effect.

The latter development is extremely significant in the field of veterinary science where developing immunological homogeneity of big animal populations is one of the basic requirements for attaining the goal that livestock should produce a level of production corresponding to the genetic capacity thereof.

In the course of our experiments for studying the immunity stimulating effect of certain compounds it has been found that the compounds of the general Formula I favourably influence the cellular protective power of the organism and on expedient application can increase the immunogenic effect of some types of herpes virus vaccines having only weak immunogenic effect (such as e.g. the vaccine used against Aujeszky's disease).

The results regarding the immunity stimulating effect of the compounds of the general Formula I obtained by model tests carried out on mice and swine are shown in Tables 1 and 2.

TABLE 1

| | Model test on mice | | | |
|---|---|---|---|---|
| Test compound 0.1 mg/mouse | Vaccine | No. of animals | RCF | CT |
| Example 2 | Ay. att. | 80 | 6–20/4–12 | 18–8/8–6 |
| | Ay. inact. | 80 | 3–17/3–9 | 7–16/6–8 |
| Example 5 | Ay. att. | 50 | 5–15/5–10 | 8–5/7–4 |
| Example 7 | Ay. att. | 50 | 7–21/5–11 | 18–10/7–4 |
| Example 3 | B$_{19}$ | 160 | 12–23/6–12 | 21–6/9–6 |
| Example 12 | Ay. att. | 50 | 4–20/3–10 | 14–6/6–4 |

Remark:
The numerator contains the values of the samples taken from animals treated with the vaccine combinated with the test compound in the 1st, 3rd, and 4th week, the denominator comprises those of the animals treated only with the vaccine; all values expressed in percent.
Legend:
RCF = Immuno-rossette development
CT = Cytotoxic reactions

TABLE 2

| | Model test on swine | | | |
|---|---|---|---|---|
| Test compound | Vaccine | No. of animals | RCF | CT |
| Example 2 | Attenuated | 10 | 14–24/6–14 | 18–13/5–11 |
| 5 mg/pig | Inactive | 10 | 5–26/4–15 | 5–21/4–11 |

Legend: See Table 1.

For in vitro reactions of the peripheral lymphocytes the following examination method has been applied:

SEPARATION OF LYMPHOCYTES

Leucocytes were separated from blood samples treated with heparine as anti-coagulant by Ficoll Paque. Cell density was adjusted to $10^6$/ml in Hanks solution containing 10% of foetal serum. From the cell suspensions 1.5 ml each was metered in Leighton-tubes and then complemented with antigens in accordance with the tests.

IMMUNOROSSETTE DEVELOPMENT (RCF)

After adequate pre-treatment a 3-percent solution of sheep red blood cells was adsorbed with Boiven's antigens. 0.1 ml of the so treated red blood cells was added to the Leighton-tubes and after a 16-hour incubation the ratio of the rossette-developing cells was microscopically evaluated in coloured preparations.

CYTOTOXIC REACTIONS (CT)

The test was carried out in an allogenic system. 0.1 ml of a lymphocyte suspension of $10^6$/ml cellular density was added to the suspension of sheep red blood cells, sensitized with antigens. The values of cytotoxic capacity were determined on the basis of haemolysis that followed a 16-hour incubation and were measured on a Spekol instrument at 540 nm. The magnitude of the reaction is expressed in the ratio compared to the controls, in percent.

As it is shown by the data of the Tables, the test compounds do not influence significantly the blastogenesis of the lymphocytes, but they increase the effectivity of the cellular immunity reactions which can be indicated in the immuno-inductive phase, by an 8–11% increase of the RCF and a 10–12% increase of the CT value.

Comparing the effect of the compounds of the general Formula I to that of the compound marked TEI-3096 described in the periodical "Drugs of the Future" (1984, 9 591), the difference resides in the fact that while the latter activates only the T suppressor cells, the compounds of the general Formula enhance the activity of the T-killer lymphocytes and also that of other so-called lymphocite-K cells and this reveals itself in the increase of the cytotoxic capacity of the cellular immunizing system.

According to a further aspect of the present invention there are provided pharmaceutial compositions comprising as active ingredient at least one compound of the general Formula I or a pharmaceutically acceptable acid addition salt thereof or a hydrate of a compound of the general Formula I or a salt thereof in admixture with suitable inert solid or liquid pharmaceutical carriers.

The pharmaceutical compositions according to the present invention can be prepared by methods known per se for the manufacture of compositions acting on the immune system. Thus the vaccine and the compound of the general Formula I can be introduced at various sites into the organism. One may also proceed by using the compound of the general Formula I in a form incorporated into a vaccine.

Further details of the present invention are to be found in the following Examples without limiting the scope of protection to the said Examples.

The daily dosage of the compounds of the general Formula I varies between wide ranges. The daily parenteral dose amounts generally to from about 0.1 mg/kg to about 30 mg/kg, preferably about 0.3–15 mg/kg, particularly about 1-2 mg/kg, on swine. The active ingredient may preferably incorporated into the vaccine and injected into the muscle. The above doses are but of informative character and the administered dose may also be above or below the above limits.

I. COMPOUNDS OF THE GENERAL FORMULA IV

Example 1

E-2-(2-Bromo-vinyl)-thio-4,6-diamino-pyrimidine

A mixture of 14.2 g (0.1 mole) of 2-mercapto-4,6-diamino-pyrimidine, 20.4 g (0.11 mole) of 1,2-dibromo-ethylene (cis+trans), 200 ml of dimethyl formamide and 13.8 g (0.1 mole) of potassium carbonate is stirred at 45° C. for 17 hours, whereupon the reaction mixture is poured into 1000 ml of water. The precipitated crystals are filtered, washed with water and dried. Thus 11.0 g of the desired compound are obtained, yield 44.5%. m.p.: 184°–186° C.

| $C_6H_7BrN_4S = 247.12$ | | |
| --- | --- | --- |
| Elementary analysis | calculated | found |
| C | 29.16% | 29.99% |
| H | 2.85% | 3.00% |
| N | 22.67% | 21.91% |
| S | 12.97% | 12.83% |
| Br$^-$ | 32.34% | 32.32% |

II. COMPOUNDS OF THE GENERAL FORMULA I

Example 2

7-Amino-5-imino-2,3-dihydro-5H-thiazol[3,2-a]pyrimidine-hydrochloride

A mixture of 14.2 g (0.1 mole) of 2-mercapto-4,6-diamino-pyrimidine, 21.6 g (0.115 mole) of ethylene bromide, (1,2-dibromo-ethylene), 200 ml of dimethyl formamide and 13.8 g (0.1 mole) of potassium carbonate is stirred at 70° C. for 5 hours. The reaction mixture is cooled, the precipitated product is filtered, washed with water and dried. Thus 23.6 g of the desired compound are obtained, yield 95%. m.p.: above 300° C.

| $C_6H_9BrN_4S = 249.136$ | | |
| --- | --- | --- |
| Elementary analysis | calculated | found |
| C | 28.93% | 28.88% |
| H | 3.64% | 3.68% |
| N | 22.49% | 22.66% |
| S | 12.87% | 12.70% |
| Br$^-$ | 32.07% | 32.08% |

Example 3

8-Amino-6-imino-3,4-dihydro-2H,6H-pyrimido[2,1-b][1,3]thiazine-hydrobromide

Method A 14.2 g (0.1 mole) of 2-mercapto-4,6-diamino-pyrimidine and 23.2 g (0.115 mole) of 1,3-dibromo-propane are reacted in an analogous manner to Example 1. The reaction mixture is worked up as described in Example 1. Thus 23.7 g of the desired compound are obtained, yield 90%. m.p.: above 300° C.

| $C_7H_{11}BrN_4S = 263.163$ | | |
| --- | --- | --- |
| Elementary analysis | calculated | found |
| C | 31.95% | 32.38% |
| H | 4.21% | 4.24% |
| N | 21.29% | 21.10% |
| S | 12.18% | 12.04% |
| Br$^-$ | 30.36% | 30.76% |

Method B 14.2 g (0.1 mole) of 2-mercapto-4,6-diamino-pyrimidine and 15.8 g (0.1 mole) of 1,3-chloro-bromo-propane are reacted in an analogous manner to Example 1. The reaction mixture is worked up as described in Example 1. Thus 17.1 g of the desired compound are obtained. Yield 65%, m.p.: above 300° C.

| $C_7H_{11}BrN_4S = 263.163$ | | |
| --- | --- | --- |
| Elementary analysis | calculated | found |
| C | 31.95% | 33.18% |
| H | 4.21% | 4.52% |
| N | 21.29% | 21.28% |
| S | 12.18% | 12.10% |
| Br$^-$ | 30.36% | 30.85% |

Example 4

7-Amino-2-phenyl-5-imino-2,3-dihydro-5H-thiazolo[3,2-a]pyrimidine-hydrobromide

A mixture of 14.2 g (0.1 mole) of 2-mercapto-4,6-diamino-pyrimidine, 30.4 g (0.115 mole) of (1,2-dibromo-ethyl)-benzene, 200 ml of dimethyl formamide and 13.8 g (0.1 mole) of potassium carbonate is stirred at 45° C. for 6 hours. The reaction mixture is cooled, the precipitate is filtered, washed with water and dried. Thus 26.0 g of the desired compound are obtained, yield 80%, m.p.: above 300° C.

| $C_{12}H_{13}BrN_4S = 325.235$ | | |
| --- | --- | --- |
| Elementary analysis | calculated | found |
| C | 44.32% | 44.52% |
| H | 4.03% | 4.04% |
| N | 17.23% | 17.10% |
| S | 9.85% | 9.81% |
| Br$^-$ | 24.57% | 25.05% |

Example 5

8-Amino-6-imino-3-methyl-2H,6H-pyrimido[2,1-b][1,3]thiazine-hydrobromide 14.2 g (0.1 mole) of 2-mercapto-4,6-diamino-pyrimidine and 19.7 g (0.115 mole) of 2-methyl-1,3-chloro-bromo-propane are reacted in an analogous manner to Example 1. The reaction mixture is worked up as described in Example 1. Thus 18 g of the desired compound are obtained, yield 65%, m.p.: above 300° C.

| $C_8H_{13}BrN_4S = 277.19$ | | |
| --- | --- | --- |
| Elementary analysis | calculated | found |
| C | 34.67% | 34.68% |
| H | 4.73% | 4.80% |
| N | 20.21% | 19.96% |
| S | 11.57% | 11.40% |

-continued

| $C_8H_{13}BrN_4S = 277.19$ | | |
|---|---|---|
| Elementary analysis | calculated | found |
| Br⁻ | 28.83% | 29.39% |

Example 6

7-Amino-5-imino-3-(or 2-)methyl-2H,5H-thiazolo[3,2-a]pyrimidine-hydrobromide 14.2 g (0.1 mole) of 2-mercapto-4,6-diamino-pyrimidine and 23.2 g (0.115 mole) of 1,2-dibromo-propane are reacted in an analogous manner to Example 1. The reaction mixture is worked up as described in Example 1. Thus 15.8 g of the desired compound are obtained, yield 60%. m.p.: above 300° C.

| $C_7H_{11}BrN_4S = 263.163$ | | |
|---|---|---|
| Elementary analysis | calculated | found |
| C | 31.95% | 32.50% |
| H | 4.21% | 4.47% |
| N | 21.29% | 21.24% |
| S | 12.18% | 11.97% |
| Br⁻ | 30.36% | 30.79% |

Example 7

N-Ethyl-N'-(5-imino-2,3-dihydro-5H-thiazolo[3,2-a]pyrimidine-7-yl)-thiourea-hydrochloride To a suspension of 26.5 g (0.1 mole) of 7-amino-5-imino-2,3-dihydro-5H-thiazolo[3,2-a]pyrimidine-hydrocarbonate-dihydrate and 140 ml of ethanol 11.3 g (0.13 mole) of ethyl isocyanate are added. The reaction mixture is heated to boiling for 90 minutes, then cooled, the precipitate is filtered, washed with ethanol and dried. Thus 23 g of N-ethyl-N'-(5-imino-2,3-dihydro-5H-thiazolo[3,2-a]pyrimidine-7-yl)-thiourea are obtained, yield 90%.

12.8 g (0.05 mole) of the above base are dissolved in 80 ml of acetone whereupon ethanol comprising an equimolar amount of hydrogen chloride is added. The reaction mixture is stirred at room temperature for an hour, filtered, washed with acetone and dried. Thus 14.6 g of the desired compound (salt) are obtained, yield 100%, m.p.: above 360° C.

| $C_9H_{14}ClN_5S_2 = 291.826$ | | |
|---|---|---|
| Elementary analysis | calculated | found |
| C | 37.04% | 37.88% |
| H | 4.83% | 4.93% |
| N | 24.00% | 23.70% |
| S | 21.97% | 21.95% |
| Cl | 12.15% | 12.10% |

Example 8

7-Amino-5-imino-2,3-dihydro-5H-thiazolo[3,2-a]pyrimidine-hydrocarbonate-dihydrate To a solution of 224 g of sodium hydrogen carbonate and 2500 ml of water 24.9 g (0.1 mole) of 7-amino-5-imino-2,3-dihydro-5H-thiazolo[3,2-a]pyrimidine-hydrobromide are added. The reaction mixture is stirred at room temperature for 8 hours, filtered, washed with water and dried. Thus 17.2 g of the desired compound are obtained, yield 75%. m.p.: 146°-148° C.

| $C_7H_{13}N_4O_5S = 265.266$ | | |
|---|---|---|
| Elementary analysis | calculated | found |
| C | 31.70% | 32.68% |
| H | 4.94% | 4.70% |
| N | 21.12% | 20.69% |
| S | 12.09% | 12.18% |

Example 9

8-Amino-6-imino-3,4-dihydro-2H,6H-pyrimido[2,1-b]thiazine-hydrocarbonate dihydrate 26.3 g (0.1 mole) of 8-amino-6-imino-3,4-dihydro-2H,6H-pyrimido[2,1-b]thiazine-hydrobromide are treated in an analogous manner to Example 8. Thus 17 g of the desired compound are obtained yield 70%. m.p.: 196°-198° C.

| $C_8H_{15}N_4O_5S = 279.293$ | | |
|---|---|---|
| Elementary analysis | calculated | found |
| C | 34.40% | 35.65% |
| H | 5.41% | 5.52% |
| N | 20.06% | 19.57% |
| S | 11.48% | 11.32% |

Example 10

7-Amino-5-imino-2,3-dihydro-5H-thiazolo[3,2-a]pyrimidine-diacetate 5.3 g (0.02 mole) of 7-amino-5-imino-2,3-dihydro-5H-thiazolo[3,2-a]pyrimidine-hydrocarbonate-dihydrate are stirred in 30 ml of acetic acid for 6 hours. The solution is evaporated, the residual crystals are suspended in ethanol, the slurry is filtered and dried. Thus 3.6 g of the desired compound are obtained, yield 59.5%, m.p.: 158°-160° C.

| $C_{11}H_{18}N_4O_4S = 320.351$ | | |
|---|---|---|
| Elementary analysis | calculated | found |
| C | 43.70% | 43.68% |
| H | 6.00% | 5.97% |
| N | 18.53% | 18.17% |
| S | 10.60% | 10.56% |

Example 11

7-Amino-5-imino-5H-thiazolo[3,2-a]pyrimidine-hydrobromide-hydrate

A solution of 12.35 g (0.05 mole) of E-2-(2-bromovinyl)-thio-4,6-diamino-pyrimidine and 50 ml of dimethyl formamide is stirred at 150° C. for 20 minutes. The solution is cooled to 0° C., the precipitate is filtered, washed with isopropanol and dried. Thus 9.5 g of the desired compound are obtained, yield 72%, m.p.: above 300° C.

| $C_6H_9BrN_4OS = 265.135$ | | |
|---|---|---|
| Elementary analysis | calculated | found |
| C | 27.18% | 27.27% |
| H | 3.42% | 3.31% |
| N | 21.18% | 20.32% |
| S | 12.09% | 11.75% |

| $C_6H_9BrN_4OS = 265.135$ | | |
|---|---|---|
| Elementary analysis | calculated | found |
| Br⁻ | 30.14% | 30.84% |

Example 12

7-Acetylamino-5-acetylimino-2,3-dihydro-5H-thiazolo[3,2-a]pyrimidine-hydrochloride A mixture of 26.5 g (0.1 mole) of 7-amino-5-imino-2,3-dihydro-5H-thiazolo[3,2-a]pyrimidine-hydrocarbonate-dihydrate and 260 ml of acetic anhydride is refluxed for an hour. The reaction mixture is cooled, the precipitate is filtered. Thus 17.7 g of 7-acetylamino-5-acetylimino-2,3-dihydro-5H-thiazolo3,2-a]pyrimidine are obtained, yield 70%.

12.6 g (0.05 mole) of the above base are dissolved in 210 ml of ethyl acetate whereupon isopropanol containing an equimolar amount of hydrogen chloride is added. The reaction mixture is stirred at room temperature for an hour, filtered, washed with ethyl acetate and dried. Thus 13.0 g of the desired salt are obtained, yield 90%. m.p.: above 300° C.

| $C_{10}H_{13}ClN_4O_2S = 288.752$ | | |
|---|---|---|
| Elementary analysis | calculated | found |
| C | 41.59% | 42.22% |
| H | 5.54% | 4.60% |
| N | 19.40% | 19.25% |
| S | 11.10% | 10.96% |
| Cl⁻ | 12.28% | 12.42% |

Example 13

7-Amino-5-imino-2,3-dihydro-5H-thiazolo[3,2-a]pyrimidine-hydrobromide

A mixture of 10.21 g (0.1 mole) of 2-amino-thiazoline, 6.61 g (0.1 mole) of malonic dinitrile, 10.12 g (0.1 mole) of trimethyl amine and 125 ml of ethanol is reacted at room temperature for 2 days. The reaction mixture is clarified and the pH is adjusted to 6 by adding 48% hydrogen bromide under cooling with ice-water. Thus 18 g of the desired compound are obtained, yield 72%, m.p.: above 300° C.

| $C_9H_9BrN_4S = 249.136$ | | |
|---|---|---|
| Elementary analysis | calculated | found |
| C | 28.93% | 29.23% |
| H | 3.64% | 3.70% |
| N | 22.49% | 22.46% |
| S | 12.87% | 12.85% |
| Br⁻ | 32.07% | 32.30% |

Example 14

7-Amino-5-imino-2,3-dihydro-5H-thiazolo[3,2-a]pyrimidine

A mixture of 10.21 g (0.1 mole) of 2-amino-thiazoline, 6.61 g (0.1 mole) of malonic dinitrile and 200 ml of dimethyl formamide is reacted at 155° C. for 20 minutes. The reaction mixture is cooled to room temperature, clarified and evaporated. The oily residue is crystallized from acetonitrile and filtered. Thus 5.1 g of the desired compound are obtained, yield 30%. m.p.: above 300° C.

| $C_6H_8N_4S = 168.218$ | | |
|---|---|---|
| Elementary analysis | calculated | found |
| C | 42.84% | 42.81% |
| H | 4.79% | 4.69% |
| N | 33.31% | 33.29% |
| S | 19.06% | 19.03% |

Example 15

9-Amino-7-imino-2,3,4,5-tetrahydro-7H-thiazepino[1,3][3,2-a]pyrimidine-hydrobromide A mixture of 14.2 g (0.1 mole) of 2-mercapto-4,6-diamino-pyrimidine, 24.8 g (0.15 mole) of 1.3 1,4-dibromo-butane, 200 ml of dimethyl formamide and 13.8 g (0.1 mole) of potassium carbonate is stirred at 80° C. for 11 hours. The precipitated inorganic salt is filtered off, the reaction mixture is clarified, evaporated and cooled to 10° C. The precipitated product is filtered, washed with isopropanol and dried. Thus 23.3 g of the desired compound are obtained, yield 84%. If necessary, the product can be recrystallized from a ten-fold amount of 50% aqueous ethanol. m.p.: 283°-284° C.

| $C_8H_{13}BrN_4S = 277.19$ | | |
|---|---|---|
| Elementary analysis | calculated | found |
| C | 34.66% | 34.65% |
| H | 4.73% | 4.76% |
| N | 20.21% | 19.58% |
| S | 11.57% | 11.35% |
| Br⁻ | 28.83% | 28.19% |

Example 16

N-Allyl-N'-(5-imino-2,3-dihydro-5H-thiazolo[3,2-a]pyrimidine-7-yl)-thiourea

A mixture of 26.5 g (0.1 mole) of 7-amino-5-imino-2,3-dihydro-5H-thiazolo[3,2-a]pyrimidine-hydrocarbonate-dihydrate and 14.87 g (0.15 mole) of allyl isothiocyanate in 200 ml of ethanol is heated to boiling for one hour and a half. The reaction having been completed, the reaction mixture is cooled to 10° C., the product is filtered, washed with cold ethanol and dried. Thus 25.75 g of the desired compound are obtained, yield 96.32%. On recrystallizing the product from 420 ml of a 4:1 mixture of dimethyl formamide and water 21.4 g of the product are obtained, m.p.: 225°-226° C.

| $C_{10}H_{13}N_5S_2 = 267.38$ | | |
|---|---|---|
| Elementary analysis | calculated | found |
| C | 44.92% | 45.70% |
| H | 4.90% | 5.10% |
| N | 26.19% | 26.25% |
| S | 23.98% | 23.30% | to a suspension of 13.37 g (0.05 mole) of the above base in 100 ml of isopropanol a mixture of isopropanol containing an equimolar amount of hydrogen chloride is added dropwise at 10° C. under stirring. The reaction mixture is stirred at this temperature for 2 hours, filtered, washed with some cold isopropanol and dried.

Thus 15.19 g of the hydrochloride of the aimed compound are obtained, yield 100%, m.p.: 186°–187° C.

| $C_{10}H_{14}ClN_5S_2 = 303.84$ | | |
|---|---|---|
| Elementary analysis | calculated | found |
| S | 39.53% | 39.47% |
| H | 4.64% | 4.58% |
| N | 23.05% | 22.95% |
| S | 21.11% | 21.15% |
| Cl⁻ | 11.67% | 11.70% |

Example 17

N-Phenyl-N'-(5-imino-2,3-dihydro-5H-thiazolo[3,2-a]pyrimidine-7-yl)-thiourea

A mixture of 26.5 g (0.1 mole) of 7-amino-5-imino-2,3-dihydro-5H-thiazolo[3,2-a]pyrimidine-hydrocarbonate-dihydrate and 20.3 g (0.15 mole) of phenyl isothiocyanate is reacted as described in Example 16 for 35 minutes. The reaction mixture is worked up. 30 g of the desired compound are obtained, yield 98.88%. The product can be recrystallized from ethanol, if necessary, m.p.: 209°–210° C.

| $C_{13}H_{13}N_5S_2 = 303.413$ | | |
|---|---|---|
| Elementary analysis | calculated | found |
| C | 51.46% | 51.37% |
| H | 4.32% | 4.41% |
| N | 23.08% | 22.29% |
| S | 21.14% | 21.04% |

From 15.17 g (0.05 mole) of the above base hydrochloride is formed as described in Example 16. Yield 16.99 g (100%), m.p.: 178°–179° C.

| $C_{13}H_{14}ClN_5S_2 = 339.913$ | | |
|---|---|---|
| Elementary analysis | calculated | found |
| C | 45.94% | 45.89% |
| H | 4.15% | 4.10% |
| N | 20.60% | 20.57% |
| S | 18.87% | 18.85% |
| Cl⁻ | 10.43% | 10.39% |

Example 18

N-Benzyl-N'-(5-imino-2,3-dihydro-5H-thiazolo[3,2-a]pyrimidine-7-yl)-thiourea

A mixture of 26.5 g (0.1 mole) of 7-amino-5-imino-2,3-dihydro-5H-thiazolo[3,2-a]pyrimidine-hydrocarbonate-dihydrate and 22.4 g (0.15 mole) of benzyl isocyanate is reacted as described in Example 17. After working up the reaction mixture 31.2 g of the desired compound are obtained, yield 98.8%. The product can be recrystallized from ethanol, if necessary, m.p.: 210°–211° C.

| $C_{14}H_{15}N_5S_2 = 317.440$ | | |
|---|---|---|
| Elementary analysis | calculated | found |
| C | 52.97% | 52.63% |
| H | 4.77% | 4.65% |
| N | 22.06% | 21.27% |
| S | 20.20% | 20.17% |

From 15.87 g (0.05 mole) of the above base hydrochloride is formed as described in Example 16. Yield 17.69 g (100%), m.p.: 201°–202° C.

| $C_{14}H_{16}ClN_5S_2 = 353.898$ | | |
|---|---|---|
| Elementary analysis | calculated | found |
| C | 47.52% | 47.48% |
| N | 4.56% | 4.53% |
| N | 19.79% | 19.74% |
| S | 18.12% | 17.94% |
| Cl⁻ | 10.02% | 9.97% |

Example 19

N-Allyl-N'-(6-imino-3,4-dihydro-2H,6H-pyrimido[2,1-b][1,3]thiazine-8-yl)-thiourea A mixture of 27.9 g (0.1 mole) of 8-amino-6-imino-3,4-dihydro-2H,6H-pyrimido[2,1-b][1,3]thiazine-hydrocarbonate-dihydrate and 14.87 g (0.15 mole) of allyl isothiocyanate is reacted as described in Example 14. The reaction mixture is worked up. Thus 28.0 g of the desired compound are obtained, yield 99.5%. The product can be recrystallized from ethanol, if necessary. m.p.: 196°–197° C.

| $C_{11}H_{15}N_5S_2 = 281.407$ | | |
|---|---|---|
| Elementary analysis | calculated | found |
| C | 46.95% | 47.39% |
| H | 5.37% | 5.41% |
| N | 24.89% | 24.70% |
| S | 22.79% | 22.69% |

From 14.07 g (0.05 mole) of the above base hydrochloride is formed as described in Example 16. Yield 15.8 g (100%), m.p.: 175°–176° C.

| $C_{11}H_{16}ClN_5S_2 = 317.907$ | | |
|---|---|---|
| Elementary analysis | calculated | found |
| C | 41.56% | 41.52% |
| H | 5.07% | 4.95% |
| N | 22.03% | 21.97% |
| S | 20.17% | 19.98% |
| Cl⁻ | 11.15% | 11.21% |

Example 20

N-Phenyl-N'-(6-imino-3,4-dihydro-2H,6H-pyrimido[2,1-b][1,3]thiazine-8-yl)-thiourea A mixture of 27.9 g (0.1 mole) of 8-amino-6-imino-3,4-dihydro-2H,6H-pyrimido[2,1-b][1,3]thiazine-hydrocarbonate-dihydrate and 20.3 g (0.15 mole) of phenyl isothiocyanate is reacted as described in Example 16 for 2 hours. The reaction mixture is worked up. Thus 31.68 g of the desired compound are obtained, yield 99.81%. m.p.: 215°–216° C.

| $C_{14}H_{15}N_5S_2 = 317.44$ | | |
|---|---|---|
| Elementary analysis | calculated | found |
| C | 52.97% | 51.68% |
| H | 4.76% | 4.67% |
| N | 22.06% | 21.57% |
| S | 20.20% | 20.23% |

15.87 g (0.05 mole) of the above base are converted into the hydrochloride as described in Example 16. Yield 17.60 g (100%). m.p.: 157°–158° C.

| $C_{14}H_{16}ClN_5S_2$ = 353.898 | | |
|---|---|---|
| Elementary analysis | calculated | found |
| C | 47.52% | 47.85% |
| H | 4.56% | 4.59% |
| N | 19.79% | 19.63% |
| S | 18.12% | 17.98% |
| Cl | 10.02% | 9.89% |

Example 21

N-Benzyl-N'-(6-imino-3,4-dihydro-2H,6H-pyrimido[2,1-b][1,3]thiazine-8-yl)-thiourea A mixture of 27.9 g (0.1 mole) of 8-amino-6-imino-3,4-dihydro-2H,6H-pyrimido[2,1-b][1,3]thiazine-hydrocarbonate-dihydrate and 22.4 g (0.15 mole) of benzyl isothiocyanate is reacted as described in Example 16 for 45 minutes. The reaction mixture is worked up. Thus 32.98 g of the desired compound are obtained, yield 99.5%. The product can be recrystallized from ethanol, if necessary. m.p.: 210°–211° C.

| $C_{15}H_{17}N_5S_2$ = 331.466 | | |
|---|---|---|
| Elementary analysis | calculated | found |
| C | 54.35% | 54.28% |
| H | 5.17% | 5.07% |
| N | 21.13% | 20.98% |
| S | 19.35% | 19.22% |

16.57 g (0.05 mole) of the above base are converted into the hydrochloride. Yield 18.35 g (100%). m.p.: 189°–190° C.

| $C_{15}H_{18}ClN_5S_2$ = 367.924 | | |
|---|---|---|
| Elementary analysis | calculated | found |
| C | 48.97% | 48.67% |
| H | 4.93% | 5.03% |
| N | 19.03% | 18.97% |
| S | 17.43% | 16.93% |
| Cl⁻ | 9.64% | 9.43% |

What we claim is:

1. A condensed pyrimidine compound of the formula I

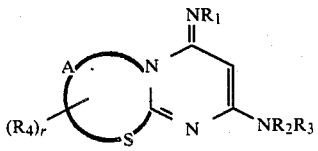

wherein

A is —CH$_2$—CH$_2$—, —CH$_2$—CH$_2$—CH$_2$, —CH$_2$—CH$_2$—CH$_2$—CH$_2$—, —CH=CH—, or one of said groups in which a hydrogen is replaced by R$_4$;

R$_4$ is C$_{1-4}$ alkyl or unsubstituted or halo, nitro, lower alkyl or lower alkoxy substituted phenyl;

r is 0, 1, 2, 3 or 4;

R$_1$ is hydrogen or C$_{1-5}$ alkanoyl;

R$_2$ is hydrogen, C$_{1-5}$ alkanoyl or a group of the formula (a)

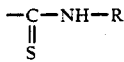

wherein

R is hydrogen, C$_{1-4}$ alkyl, C$_{2-4}$ alkenyl, phenyl or phenyl-C$_{1-3}$ alkyl and R$_3$ is hydrogen or a pharmaceutically acceptable acid addition salt thereof or a hydrate of a compound of the formula I or a acid addition salt thereof.

2. A compound of the formula I as defined in claim 1, wherein A i —CH$_2$—CH$_2$— or CH$_2$—CH$_2$—CH$_2$— or said groups in which a hydrogen is replaced by methyl; r is 1; R$_1$ and R$_3$ are each hydrogen and R$_2$ is hydrogen or a group of the formula (a), in which R is ethyl.

3. A compound of the formula I as defined in claim 1 which is 7-amino-5-imino-2,3-dihydro-5H-thiazolo[3,2-a]pyrimidine;

8-amino-6imino-3,4-dihydro-2H,6H-pyrimido[2,1-b][1,3]-thiazine;

8-amino-6-imino-3-methyl-2H,6H-pyrimido[2,1-b][1,3]-thiazine;

N-ethyl-N'-(5-imino-2,3-dihydro-5H-thiazolo[3,2-a]pyrimidine-7-yl)-thiourea;

7-acetylamino-5-acetylimino-2,3-dihydro-5H-thiazol[3,2-a]pyrimidine;

or a pharmaceutically acceptable acid addition salt thereof.

4. A pharmaceutical composition having immunostimulating properties which comprises: an effective amount of a compound of the formula I as defined in claim 1 as an active agent and a pharmaceutically acceptable carrier or diluent therefor.

5. A pharmaceutical composition as defined in claim 4, wherein the active agent is 7-amino-5-imino-2,3-dihydro-5H-thiazolo[3,2-a]pyrimidine; 8-amino-6-imino-3,4-dihydro-2H,6H-pyrimido[2,1-b][1,3]-thiazine; 8-amino-6-imino-3-methyl-2H,6H-pyrimido[2,1-b][1,3]-thiazine; N-ethyl-N'-(5-imino-2,3-dihydro-5H-thiazolo[3,2-a]pyrimidine-7-yl)-thiourea; or 7-acetylamino-5-acetylimino-2,3-dihydro-5H-thiazol [3,2-a]pyrimidine.

6. A pharmaceutical composition as defined in claim 4, wherein the active agent is 7-amino-5-imino-2,3-dihydro-5H-thiazolo[3,2-a] pyrimidine or a pharmaceutically acceptable acid addition salt thereof.

7. A pharmaceutical composition as defined in claim 4, wherein the active agent is 7-amino-5-imino-2,3-dihydro-5H-thiazolo[3,2-a] pyrimidine hydrochloride.

8. A method of stimulating the immunosystem of a patient in need thereof which comprises: administering to the patient an effective amount of a compound of the formula I as defined in claim 1.

9. The method of claim 8, wherein the compound is selected from the group consisting of 7-amino-5-imino-2,3-dihydro-5H-thiazolo[3,2-a] pyrimidine; 8-amino-6-imino-3,4-dihydro-2H,6H-pyrimido[2,1-b] [1,3]-thiazine; 8-amino-6-imino-3-methyl-2H,6H-pyrimido[2,1-b][1,3]-thiazine; N-ethyl-N'-(5-imino-2,3-dihydro-5H-thiazolo[3,2-a] pyrimidine-7-yl)-thiourea; or 7-acetylamino-5-acetylimino-2,3-dihydro-5H-thiazol [3,2-a]pyrimidine or a pharmaceutically acceptable acid addition salt thereof.

10. The method of claim 8, wherein the compound is 7-amino-5-imino-2,3-dihydro-5H-thiazolo [3,2-a] pyrimidine or a pharmaceutically acceptable acid addition salt thereof.

11. The method of claim 8, wherein the compound is 7-amino-5-imino-2,3-dihydro-5H-thiazolo [3,2-a] pyrimidine hydrochloride.

12. The compound of the formula I as defined in claim 1, which is 7-amino-5-imino-2,3-dihydro-5H-thiazolo[3,2-a] pyrimidine or a pharmaceutically acceptable acid addition salt thereof.

13. The compound of formula I as defined in claim 1, which is 7-amino-5-imino-2,3-dihydro-5H-thiazolo [3,2-a] pyrimidine hydrochloride.

* * * * *

UNITED STATES PATENT AND TRADEMARK OFFICE
CERTIFICATE OF CORRECTION

PATENT NO. : 4,921,854

DATED : May 1, 1990

INVENTOR(S) : Daniel BOZSING et al.

It is certified that error appears in the above-identified patent and that said Letters Patent is hereby corrected as shown below:

<u>Claim 2, column 18, line 13</u> that part of line 13 reading "wherein A i-$CH_2CH_2$-" should read -- where A is -$CH_2CH_2$- --

Signed and Sealed this

Eleventh Day of June, 1991

Attest:

HARRY F. MANBECK, JR.

*Attesting Officer*   *Commissioner of Patents and Trademarks*